United States Patent [19]

Wernicke et al.

[11] Patent Number: 5,188,104
[45] Date of Patent: Feb. 23, 1993

[54] TREATMENT OF EATING DISORDERS BY NERVE STIMULATION

[75] Inventors: Joachim F. Wernicke, League City; Reese S. Terry, Jr.; Ross G. Baker, Jr., both of Houston, all of Tex.

[73] Assignee: Cyberonics, Inc., Webster, Tex.

[21] Appl. No.: 649,618

[22] Filed: Feb. 1, 1991

[51] Int. Cl.$^5$ .............................................. A61N 1/05
[52] U.S. Cl. ................................ 128/419 R; 128/784; 128/785; 128/419 C; 128/421
[58] Field of Search ................ 128/784–785, 128/642, 421, 419 R, 422–423, 419 C, 400.5, 731.2

[56] References Cited

U.S. PATENT DOCUMENTS

Re. 33,420 11/1990 Sussman et al. ............... 128/419 R
4,867,164 9/1989 Zabara ............................ 128/421

Primary Examiner—Lee S. Cohen
Assistant Examiner—Brian Casler
Attorney, Agent, or Firm—Leitner, Green & Christensen

[57] ABSTRACT

A method of treating patients with compulsive eating disorders includes the steps of detecting a preselected event indicative of an imminent need for treatment of the specific eating disorder of interest, and responding to the detected occurrence of the preselected event by applying a predetermined stimulating signal to the patient's vagus nerve appropriate to alleviate the effect of the eating disorder of interest. For example, the preselected event may be a specified level of food consumption by the patient within a set interval of time, or the commencement of a customary mealtime according to the patient's circadian cycle, or the passage of each of a sequence of preset intervals of time, or the patient's own recognition of the need for treatment by voluntarily initiating the application of the stimulating signal to the vagus nerve. In cases in which the disorder is compulsive eating to excess, the stimulating signal is predetermined to produce a sensation of satiety in the patient. The occurrence of the preselected event is detected by summing the number of swallows of food by the patient within the set interval of time. In cases where the disorder is compulsive refusal to eat (anorexia nervosa), the stimulating signal is predetermined to produce a sensation of hunger or to suppress satiety in the patient.

19 Claims, 3 Drawing Sheets

TREATMENT OF EATING DISORDERS BY NERVE STIMULATION

BACKGROUND OF THE INVENTION

The present invention relates generally to methods and apparatus for treating or controlling medical, psychiatric or neurological disorders by application of modulating electrical signals to a selected nerve or nerve bundle, and more particularly to techniques for treating patients with eating disorders by application of such signals to the patient's vagus nerve with a neurostimulating device.

Treatment of obesity attributable to compulsive overeating has included many different schemes in the past. Among these is the use of ethical (or prescription) and patent (or nonprescription) drugs or other ingestible preparations designed to suppress the appetite or to induce satiety (i.e., the satisfied feeling of being full after eating). Another type of treatment employs dietary menus selected to reduce caloric intake, often combined with a regimen of routine or aerobic exercise. An increasingly popular treatment is liposuction (suction lipectomy), at one time prescribed almost exclusively only for removing adipose tissue from obese patients, but more recently enjoying wide application for cosmetic reshaping of the anatomy, particularly the abdomen, hips, thighs and buttocks of non-obese persons. In advanced or extreme cases, treatment of obesity has included more radical techniques such stapling or resectioning of the stomach, or wiring the jaws shut.

In general, these and other prior art techniques for treating compulsive overeating/obesity have tended to produce only a temporary effect. After the initial weight loss and typical plateauing of further loss, the individual usually becomes discouraged and/or depressed, and reverts to the previous behavior of compulsive overeating. The more radical techniques employed for treating the extreme cases are sufficiently drastic to warrant consideration of methods which are less intrusive and more easily tolerated by the patient. Even stomach stapling and resection have been found to produce only short term benefit.

The present invention is primarily directed to methods and devices for stimulation of the vagus nerve to treat compulsive overeating and obesity, but which may be employed to treat other, even more serious eating disorders, such as bulimia (a disorder in which the individual experiences periods of insatiable craving for food, often resulting in episodes of binge eating followed by forced vomiting) and anorexia nervosa (a neuropsychiatric disorder in which the individual suffers a prolonged and sometimes fatal refusal to eat), as well. The treatment is characterized by the application of selected electrical stimuli to the vagus nerve or a bundle of nerve fibers thereof.

Food intake is controlled by a complex interaction of internal and external stimuli. The vagus nerve plays a role in mediating afferent information from the stomach to the satiety centers of the brain. Davidson and Clarke reported in *Am. J. Physiol* (1988) 255:G55-G61, their findings that afferent vagal fibers from the stomach wall increased their firing rate when the stomach was filled. This satiety effect is known to be mediated by cholecystokinin (CCK) and pancreatic glucagon, as shown by Sauter and Geary in *J. Auton. Nerv. Syst.* (1990) 30:13-22. In *Neuropharmacol.* (1990) 29(2):109-118, Schick et al reported on experiments conducted in animals that the central receptors for CCK reside in the nucleus of the solitary tract, which are the projection sites for the vagus nerve. This is also the case in humans, as indicated by Hyde and Peroutka in their report in *Brain Res.* (1989) 495:198-202. Weatherford and Ritter, in *Physiol. and Behav.* (1988) 43:645-650, further showed that glucagon mediated satiety involves separate cells in contrast to CCK mediated satiety in the nucleus of the solitary tract and area postrema.

Peikin in *Gastroenterol. Clinics of North America* (1989) 18(4):757-775 has reviewed the role of CCK in the control of food intake, and the potential use of CCK and analogues in the treatment of eating disorders. Although the focus has been on the possibility of upmodulating CCK activity for the treatment of obesity and bulimia, decreasing CCK activity for treatment of anorexia is also a possibility.

Extra-physiologic electrical stimulation of the vagus nerve has previously been proposed for treatment of epilepsy and various forms of involuntary movement disorders. Specifically, in U.S. Pat. No. 4,702,254 issued Oct. 27, 1987 to J. Zabara (referred to herein as "the '254 patent"), a method and implantable device are disclosed for alleviating or preventing epileptic seizures, characterized by abnormal neural discharge patterns of the brain. The '254 patent describes an implantable neurocybernetic prosthesis (NCP) which utilizes neurocybernetic spectral discrimination by tuning the external current of the NCP generator to the electrochemical properties of a specific group of inhibitory neurons that affect the reticular system of the brain. These neurons are embedded within a bundle of other neurons, and are selectively activated directly or indirectly by the tuning of the NCP to augment states of brain neural discharge to control convulsions or seizures. According to the patent, the spectral discrimination analysis dictates that certain electrical parameters of the NCP pulse generator be selected based on the electrochemical properties of the nerves desired to be activated. The patent further indicates that the optimum sites for application of the NCP generator output to produce the desired effects are the cranial nerves in general, and the vagus nerve (the tenth cranial nerve) in particular.

The NCP disclosed in the '254 patent may be activated either manually or automatically, to provide treatment for the duration of the seizure. Manual activation is performed when the patient experiences the aura at onset of the seizure. Alternatively, automatic activation may be triggered upon detection of instantaneous changes in certain state parameters immediately preceding or at onset. Additionally, a "prophylactic" or preventive mode may be employed in which the NCP is activated periodically to reduce the occurrence and/or the intensity of the seizures.

The NCP stimulator of the '254 patent is implanted in the patient's chest and is connected to electrodes installed at the selected point of signal application at the nerve site with the more negative electrode situated closer to the brain and the positive electrode further from the brain, along the vagus nerve.

It is known that each nerve in the human body is composed of thousands of fibers, of different sizes designated by groups A, B and C, which carry signals to and from the brain. The vagus nerve, for example, may have approximately 100,000 fibers of the three different sizes, each carrying signals. Each axon (fiber) only conducts in one direction, in normal circumstances. The A and B fibers are myelinated (i.e., have a myelin sheath, constituting a substance largely composed of fat), whereas the C fibers are unmyelinated.

Myelinated fibers are typically larger, conduct faster and have very low stimulation thresholds, compared to the unmyelinated type. Very little energy is required to stimulate the myelinated fibers, and they exhibit a particular strength-duration curve or respond to a specific pulse width versus amplitude for stimulation. The A and B fibers can be stimulated with relatively narrow pulse widths, from 50 to 200 microseconds ($\mu s$), for example. The A fiber conducts slightly faster than the B fiber and has a slightly lower threshold. The C fibers are very small, conduct electrical signals very slowly, and have high stimulation thresholds typically requiring a wider pulse width (300–1000 $\mu s$) and a higher amplitude for activation. Selective stimulation of only A and B fibers is readily accomplished. The requirement of a larger and wider pulse to stimulate the C fibers, however, makes selective stimulation of only C fibers, to the exclusion of the A and B fibers, virtually unachievable inasmuch as the large signal will tend to activate the A and B fibers to some extent as well.

Usually, nerve stimulation activates signals in both directions (bidirectionally). It is possible, however, through the use of special electrodes and waveforms, to selectively stimulate a nerve in one direction only (unidirectionally).

In a paper on the effects of vagal stimulation on experimentally induced seizures in rats (Epilepsia 1990, 31 (Supp 2): S7–S19), Woodbury notes that the vagus nerve is composed of somatic and visceral afferents (inward conducting nerve fibers that convey impulses toward a nerve center such as the brain or spinal cord) and efferents (outward conducting nerve fibers that convey impulses to an effector to stimulate same and produce activity). The vast majority of vagal nerve fibers are C fibers, and a majority are visceral afferents having cell bodies lying in masses or ganglia in the neck. The central projections terminate, by and large, in the nucleus of the solitary tract which sends fibers to various regions of the brain (e.g, the hypothalamus, thalamus, and amygdala); others continue to the medial reticular formation of the medulla, the cerebellum, the nucleus cuneatus and other regions.

SUMMARY OF THE INVENTION

The invention is directed to apparatus and methods principally for treating compulsive overeating and obesity, but which may also be applied to treat other compulsive eating disorders, such as bulimia and anorexia nervosa. The treatment is carried out by selectively applying specially adapted modulating electrical signals to the patient's vagus nerve by means of a neurostimulator which is preferably totally implanted in the patient, but may alternatively be employed external to the body or even percutaneously. The modulating signals may be stimulating or inhibiting, but for purposes of this disclosure both are sometimes included herein within the term "stimulating". The present invention recognizes and employs specific techniques of vagal stimulation in a therapeutic regimen for treatment of eating disorders in general, and compulsive overeating/obesity in particular.

Neurotransmitters, classified as inhibitory or excitatory, may be generated by stimulating the vagus nerve. The vagus nerve may also be stimulated to cause more neural impulses to move up the nerve or to block neural impulses from moving up the nerve. In systems according to the present invention the modulating signals may stimulate or inhibit other neural impulses and result in excitatory or inhibitory neurotransmitter release.

Strategies for vagal modulation, which consists of adjusting the parameters for electrical stimulation of the vagus nerve (which may include, as well, inhibition or blocking of signals on the nerve, nerve fibers or nerve bundle), depend on a number of factors. These factors include a consideration of which of the nerve fibers are to be subjected to the modulation; whether the patient experiences a "feeling" or sensation at the onset of the disorder or a symptom of the disorder which can be used to activate the neurostimulation generator or, alternatively, a physiologic signal is generated which can be detected and employed to trigger the modulation; and/or whether a "carryover" or refractory period occurs after modulation in which the benefit of the modulation is maintained.

Different stimulation signal parameters can differentially stimulate various fibers. The present invention takes advantage of threshold curves to activate the various fibers of a patient's vagus nerve for selective modulation thereof, e.g., stimulation of A and B, but not C; or C, but not A and B; or A, B and C; in the treatment of the eating disorder. By appropriately setting pulse width and amplitude, for example, at the output of a neurostimulator which is applied via electrodes to the patient's vagus nerve, particular fibers of the nerve can be selectively stimulated.

Accordingly, the conditions peculiar to the individual patient, and the nerve fibers to be activated, will determine the specific details of the vagal modulation treatment. For example, because the C fibers conduct signals very slowly, they are not highly responsive to techniques of fast stimulation. The precise signal pattern to be used, such as the length of the time intervals in which the signal is on and off, will depend upon and be adjusted to the individual patient and the particular eating disorder being treated.

In the case of obesity, the treatment produces appetite suppression, resulting in decreased intake of food and consequent weight reduction, by causing the patient to experience satiety. In effect, the brain perceives the stomach to be full as a result of the treatment. Treatment of anorexia nervosa would involve the use of a stimulating signal pattern to modulate vagal activity in such a way as to enhance the patient's appetite or at least suppress satiety. Bulimia may be treated by application of an intermittent stimulation signal pattern from the neurostimulator to the vagus nerve to produce the same sensation of satiety as with treatment of the compulsively overeating obese patient.

Selective stimulation of the vagus nerve to treat and control eating disorders in general and compulsive eating disorders in particular exhibits considerably greater likelihood of success than attempts to change eating behavior by injection of CCK and pancreatic glucagon. Also, control of eating behavior may be better and more easily achieved by selective vagal modulation than by administering exogenous CCK or glucagon because these are peptides which cannot be given orally and even if given parenterally are not likely to reach their target receptors.

Sengupta et al reported in *J. Neurophysiol.* (1989) 61(5):1000–1010, that esophageal distension was associated with an afferent vagal discharge rate of approximately 30–50 Hz. Primarily C fibers and A-delta fibers (the latter being classified by the investigators as esophageal tension afferents with conduction velocities of 2.5–22 m/s) were found to mediate these impulses. The data may indicate that vagal modulation at these frequencies and a duration of ten seconds will approximate a physiological response to gastric distension.

In a preferred embodiment of the present invention for treating patients with compulsive overeating-/obesity disorders, an implantable neurostimulator has a signal generator or electronics package adapted to generate an electrical output signal, preferably in the form of a sequence of pulses, with parameter values programmable by the attending physician within predetermined ranges for treating the specified eating disorder, and has a lead/electrode system for applying the programmed output signal to the patient's vagus nerve. The overall treatment system, which in the preferred embodiment includes implanted and external electronics, is calibrated for a particular patient by telemetry from the implant. The implanted electronics package may then be externally programmed for activation upon occurrence of a predetermined detectable event, or may be periodically or continuously activated, to generate the desired output signal with parameter values programmed according to the nature of the eating disorder being treated. This output signal is applied to the patient's vagus nerve to modulate vagal activity in a predetermined manner to produce a sensation which is appropriate to control the eating behavior of the patient according to the specific nature of the disorder.

In alternative embodiments of the invention, the stimulus generator or electronics package may be external to the patient, with only an RF coil, rectifier and the lead/nerve electrode assembly implanted; or with the lead implanted percutaneously through the skin and to the nerve electrode. The latter technique requires special precautions to guard against potential infection because of the existence of a path from outside the body to the nerve along the lead, and consequently is the least preferred among those embodiments of the device and/or the method of using the device.

In use of the preferred embodiment, the stimulus generator of the neurostimulator is implanted in a convenient location in the patient's body, preferably in the abdomen in relatively close proximity to the stimulating electrode system and, if applicable, to the detecting system. In the case of treating compulsive overeating and obesity, for example, it is desirable to ascertain the patient's food intake, i.e., the quantity consumed. To that end, sensing electrodes may be implanted in or at the esophagus to detect passage of food as the patient swallows. These swallows are summed over a preselected time interval, to estimate the amount of food consumed in that interval. Modulation of vagal activity is initiated if this summation exceeds a preselected threshold level. In the preferred embodiment, the stimulating electrode (nerve electrode) is implanted about the vagus nerve or branch thereof in the esophageal region slightly above the stomach.

Thus, according to the invention, a method of treating obesity caused by overeating includes the steps of sensing the quantity of food consumed by the patient in a predetermined period of time, and, if the consumption exceeds a predetermined level in that time period, applying a stimulating signal to the patient's vagus nerve to produce or induce satiety. As a result, the patient experiences a satisfied feeling of fullness at a level of consumption sufficient to maintain physiologic needs but supportive of weight reduction. In the preferred method the signal is applied to the vagus nerve just above the stomach.

A similar method may be utilized to treat bulimia, in that the output signal parameters of the neurostimulator's stimulus generator are programmed to stimulate vagal activity in such a way as to induce a sensation of fullness of the patient's stomach, upon sensing an excessive level of food consumption (i.e., exceeding the predetermined level in the selected time interval, by integrating the number of swallows of food over that interval). Anorexia nervosa may be treated by a somewhat different method, in which the neurostimulator is programmed so that the output signal of the stimulus generator is designed to inhibit vagal activity to induce a sensation of hunger or at least to suppress satiety in the patient, preferably at normal mealtimes according to the custom or needs of the individual patient.

In another method, the appropriately programmed output signal of the neurostimulator is applied to modulate the patient's vagus nerve activity, again preferably just above the stomach, but the signal is periodically applied without regard to consumption of a particular quantity of food except at prescribed mealtimes during normal waking hours according to the patient's circadian cycle. This serves to suppress the patient's appetite (by producing the sensation of satiety) in the obese or bulimic patient between normal mealtimes.

In each of the foregoing treatment methods, the neurostimulator electronics package is automatically activated to generate a stimulating output signal appropriate (by programming) to treat the specified condition upon detecting a specific event. In the case of the obese or bulimic patient, the event may be an excessive level of food consumption within a set period, or may be set intervals between customary meal times. In the case of the anorexic patient, the event may be the commencement of his or her prescribed normal mealtime. In response to detection of the event, the neurostimulator is activated to stimulate the patient's vagus nerve.

Alternatively, or in addition to the automatic detection of the event and activation of the signal generation in response thereto, the neurostimulator electronics package may be implemented for manual activation of the output signal by the patient such as by placement of an external magnet over the implanted device (to close a switch), or by tapping the region over the device (to cause it to respond to the sound or vibration), or by use of an RF transmitter, for example. Manual activation is useful in situations where the patient has an earnest desire to control his or her eating behavior, but requires supportive measures because of a lack of sufficient will power or self-control to refrain from the compulsive behavior in the absence of the neurostimulation device of the invention. For example, the bulimic patient may voluntarily initiate the programmed vagal activity modulation therapy by means of the manual activation technique for which the device is implemented when he or she senses the urge to binge eat.

Accordingly, it is a principal object of the present invention to provide improvements in methods and apparatus for treating and controlling eating disorders.

It is a more specific object of the invention to provide methods of treating and controlling eating disorders by selective modulation of vagal activity for stimulation or inhibition thereof, or for release of excitatory or inhibitory neurotransmitters, according to the nature of the individual's eating disorder.

Another object of the invention is to provide techniques for treating and controlling eating disorders, including obesity caused by overeating, anorexia nervosa, and bulimia by applying to the patient's vagus nerve an appropriate electrical signal for controlling vagal activity.

A further object of the invention is to provide methods of and apparatus for treating and controlling eating disorders by applying electrical stimuli to the patient's vagus nerve to selectively activate a specific group of fibers of the nerve, according to the specific nature of the eating disorder.

Yet another object of the invention is to provide methods and apparatus for treating and controlling any of various compulsive eating disorders by sensing a symptom of the particular disorder and thereafter automatically or manually initiating selective modulation of vagal activity to suppress or enhance the patient's desire to eat depending on the nature of the disorder.

BRIEF DESCRIPTION OF THE DRAWINGS

The above and still further objects, aspects, features and attendant advantages of the present invention will be better understood from a consideration of the following detailed description of presently preferred methods and embodiments thereof, taken in conjunction with the accompanying drawings, in which.

DESCRIPTION OF THE PRESENTLY PREFERRED EMBODIMENT AND METHOD

Figure 1:
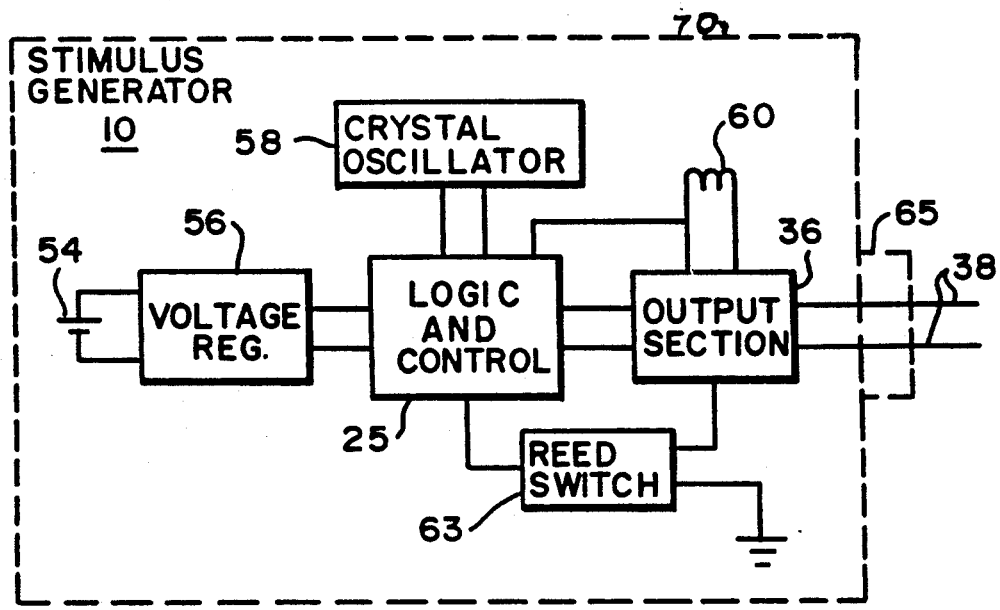
FIG. 1 is a simplified block diagram of an implantable neurostimulator electronics package (stimulus generator) for use (with appropriate parameter settings and ranges) in treating eating disorders according to the present invention.
Figure 2:
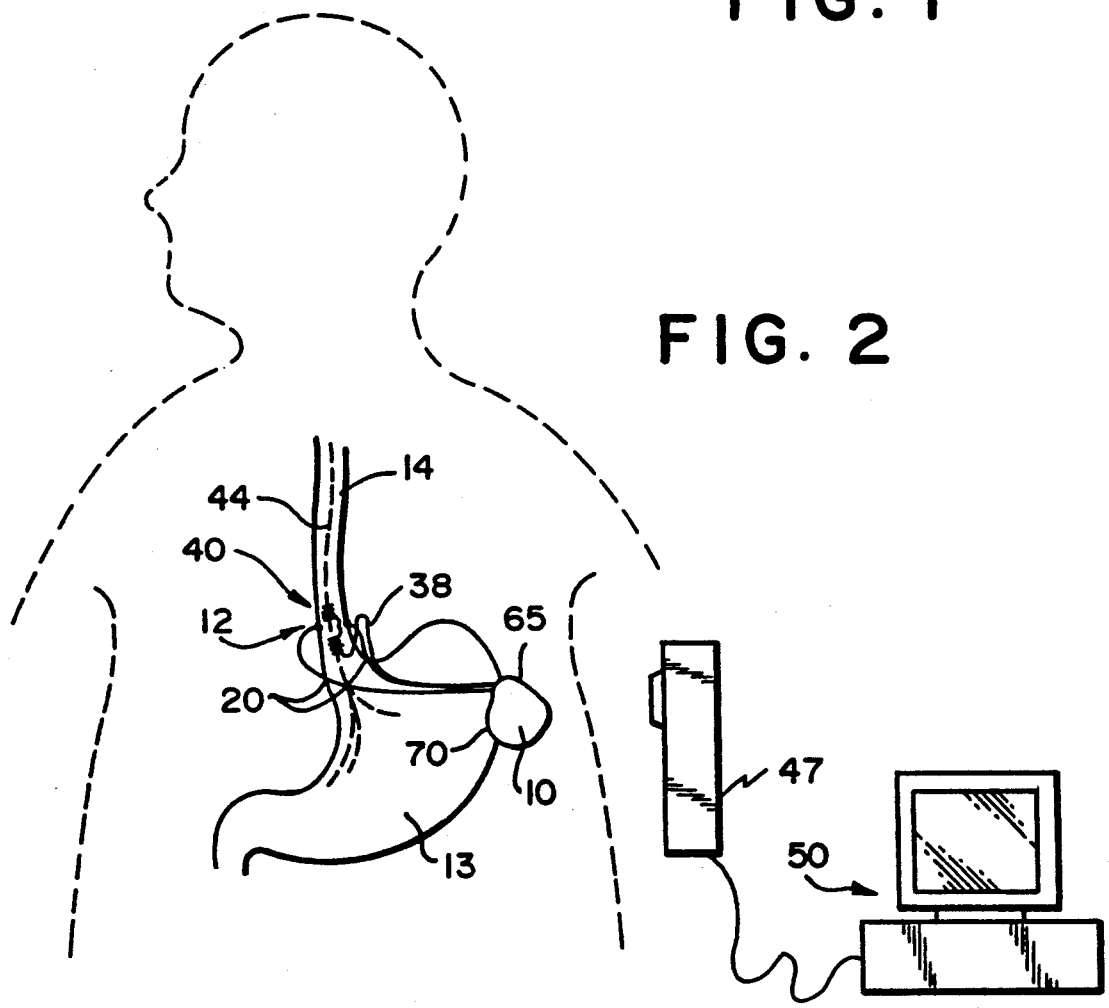
FIG. 2 is a simplified fragmentary illustration of the stimulus generator and lead/electrode system of the neurostimulator implanted in the patient's body.
Figure 3:
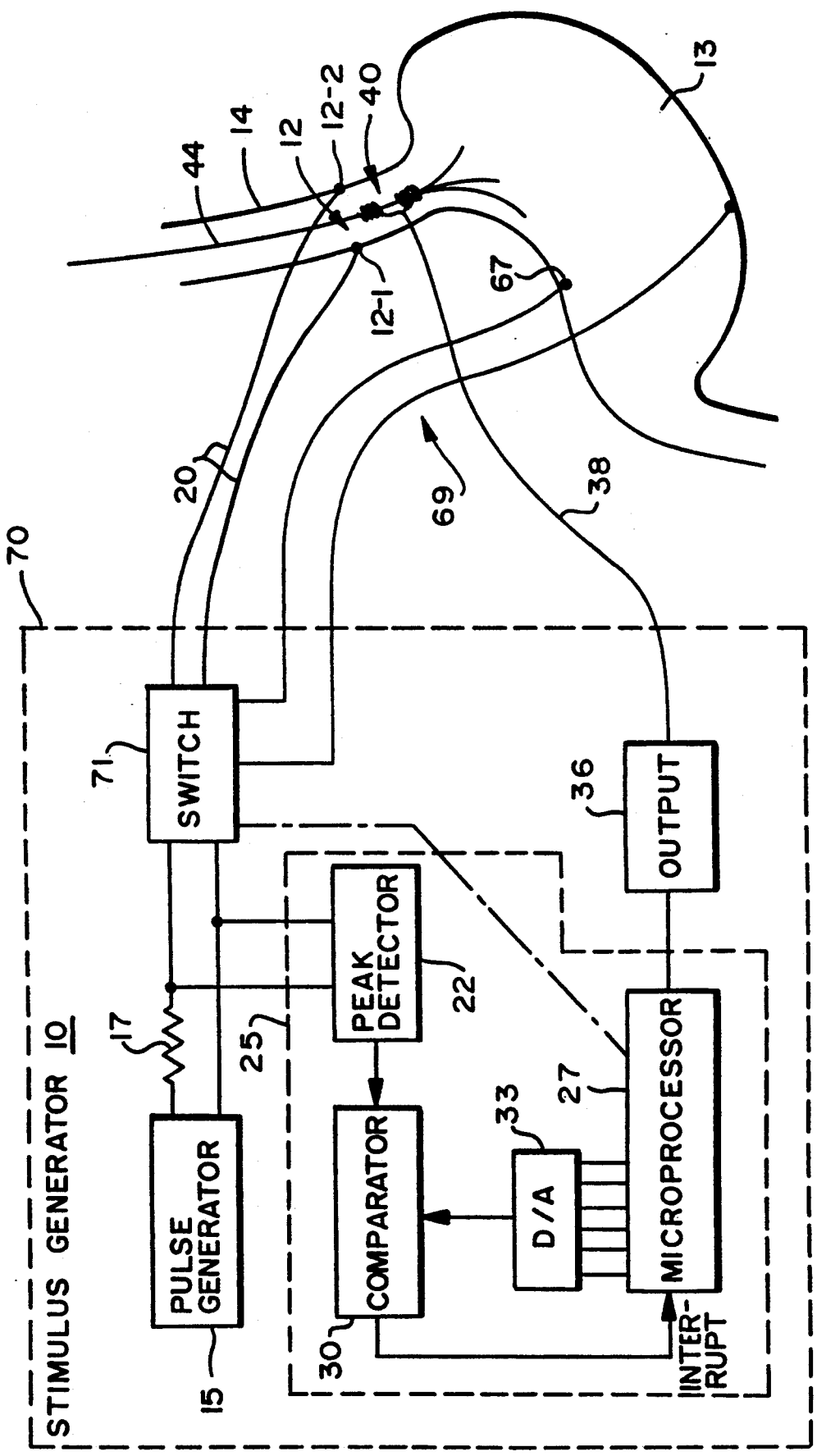
FIG. 3 is a more detailed view of a portion of the preferred embodiment of the stimulus generator and associated lead/electrode system of the neurostimulator illustrating certain exemplary details of the generator and of the placement of the detection and stimulation portions of the lead/electrode system relative to the patient's vagus nerve and stomach.
Figure 4:
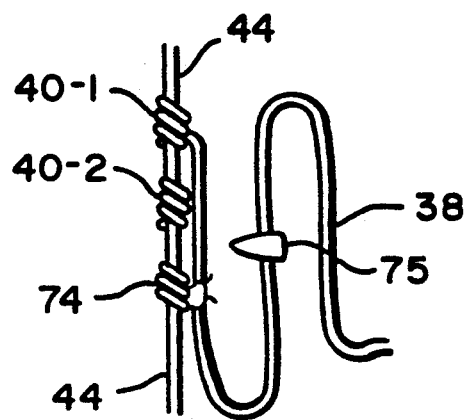
FIG. 4 is a detailed fragmentary illustration of the implanted nerve electrode for modulating vagal activity.

Referring now to the drawings, a block diagram of the basic components of the general electronics package of an implantable neurostimulator and their interrelationship is illustrated in FIG. 1, and details of location of the implanted device and of portions of the preferred embodiment of the electronics package and lead/electrode system are shown in FIGS. 2, 3 and 4. A generally suitable form of neurostimulator for use in the apparatus of the present invention is disclosed in copending U.S. patent application Ser. No. 07/434,985 of Anthony J. Varrichio et al., titled "Current Source with Programmable Overhead Voltage," filed Nov. 10, 1989 (referred to herein as "the '985 application"), assigned to the same assignee as the instant application. The specification of the '985 application is incorporated herein in its entirety by reference, but for the sake of convenience to the reader, certain portions of it are summarized in this application.

The neurostimulator utilizes a conventional microprocessor and other standard electrical and electronic components, and communicates with an external programmer and/or monitor by asynchronous serial communication for controlling or indicating states of the device. Passwords, handshakes and parity checks are employed for data integrity. The neurostimulator also includes means for conserving energy, which is important in any battery operated device and especially so where the device is implanted for medical treatment of a disorder, and means for providing various safety functions such as preventing accidental reset of the device.

A preferred embodiment of the neurostimulator according to the invention has certain material differences from the type described in detail in the '985 application, as will be described below. An electronics package in the form of stimulus generator 10 is implanted in the patient's body, preferably in a pocket formed by the implanting surgeon just below the skin in the abdomen as shown in FIG. 2. In conjunction with its microprocessor-based logic and control circuitry, stimulus generator 10 includes detection circuitry for automatically initiating the stimulating signal generation, and output circuitry for patterning the stimulating signal to modulate vagal activity in a manner designed to treat the compulsive eating disorder of interest.

The detection circuitry includes a set of implantable electrodes 12 (FIG. 2) which are coupled to the stimulus generator by a suitable electrical lead or leads 20 of known type for use in and biocompatible with implantation in the body. Electrodes 12 themselves are secured to opposite sides of the patient's esophagus 14, preferably at a site just above the stomach 13 as shown in FIGS. 2 and 3. Alternatively, they may be located in the patient's neck. Electrode set 12 may be bipolar or quadripolar, to sense the impedance between one pair or two pairs of electrodes positioned at the opposite sides of esophagus 14 generally in the same plane and normal to the length of the esophageal tube. The electrodes themselves may be composed of activated iridium, rhodium, platinum or other suitable material.

Because polarization potentials on the electrodes tend to distort the measurements, it is desirable to employ quadripolar electrodes in which one pair is used for signal generation and the other pair is used for signal sensing. Preferably, however, each of the detecting electrodes is coated with a thin layer of iridium oxide to substantially enhance its sensitivity to electrical signals, reduce polarization potentials, and rapidly dissipate the polarization potentials. If the iridium oxide coating is used, a bipolar electrode set 12-1, 12-2 is preferred (FIG. 3). Each of the electrodes may be provided with a biocompatible fabric "collar" or band about the electrode periphery to allow it to be readily sutured in place in the esophageal locations.

With reference to FIG. 3, stimulus generator 10 includes a pulse generator 15 (preferably, but an AC signal generator may alternatively be used). With a four electrode system, the pulse generator is connected via a high impedance 17 and the leads 20 to excitation electrodes, and a peak detector 22 is connected via leads 20 to sensing electrodes, among electrode set 12. The peak detector includes a low pass filter for smoothing the detected peaks over a predetermined period of time—ten seconds, for example—although the averaging period may be more or less than that as will be apparent from the description of operation set out below. The peak detector and averaging circuit are part of the logic and control section 25 of the stimulus generator electronics package (FIGS. 1 and 3). Section 25 also includes a microprocessor 27, a comparator 30 and a digital-to-analog (D/A) converter 33 (FIG. 3).

The output of the peak detector 22 is applied as one input to comparator 30, which also receives an input in the form of analog data from the D/A converter 33. Microprocessor 27, which is programmable, supplies digital inputs to the D/A converter and receives an input from comparator 30. The microprocessor supplies a control input, as an output of logic and control section 25, to an output signal generation section 36. The latter is coupled to bipolar stimulation electrode set 40 via a biocompatible electrical lead or leads 38. Stimulation electrode set 40 is secured to the patient's vagus nerve 44 (FIG. 3, and in greater detail in FIG. 4).

Components of the system for use (by the attending physician) external to the patient's body including a programming wand 47 which, among other things, communicates parameter changes to stimulus generator 10, and a computer 50 and associated software for adjustment of parameters and control of communication between the implanted electronics, the programming wand and the computer (FIG. 2).

As shown in more simplified block diagrammatic form in FIG. 1, stimulus generator 10 also includes a battery (or set of batteries) 54, which may be of any reliable long-lasting type conventionally employed for powering implantable medical electronic devices (such as batteries employed in implantable cardiac pacemakers or defibrillators). In the preferred embodiment of the stimulus generator, battery 54 is a single lithium thionyl chloride cell with its output terminals connected to the input side of voltage regulator 56. The regulator smoothes the battery output to produce a clean, steady output voltage, and provides enhancement thereof such as voltage multiplication or division if necessary for a specific application.

The regulator 56 supplies power to logic and control section 25, which controls the programmable functions of the device. Among these programmable functions are output current, output signal frequency, output signal pulse width, output signal on-time, output signal off-time, daily treatment time for periodic modulation of vagal activity), and output signal-start delay time. Such programmability allows the output signal to be selectively crafted for application to the stimulating electrode set 40 (FIG. 2) to obtain the desired modulation of vagal activity for treatment and control of the eating disorder of interest with the particular patient. Logic and control section 25 may also be implemented to control programmable functions of the pulse generator 15 (FIG. 3). Timing signals to section 25 and to pulse generator 15 are provided by a crystal oscillator 58.

Built-in antenna 60 enables communication between the implanted stimulus generator and the external electronics (including both programming and monitoring devices) to permit the device to receive programming signals for parameter changes, and to transmit telemetry information, from and to programming wand 47. Once the system is programmed, it operates continuously at the programmed settings until they are reprogrammed by means of computer 50 and programming wand.

The logic and control section controls an output circuit or section 36 of the stimulus generator, which functions to generate the programmed signal levels appropriate to the condition (eating disorder) being treated. Output section 36 and the programmed output signal thereof is coupled (directly, capacitively, or inductively) to an electrical connector 65 on the housing 70 of the generator and to the lead assembly 38 and the stimulating electrodes 40 connected thereto (FIG. 2). In this way, the programmed output signal of stimulus generator 10 is applied to the nerve electrode set implanted on the patient's vagus nerve 44, to modulate the vagal activity in a desired manner to alleviate the disorder.

A reed switch 63 (FIG. 1) permits alternative or additional manual activation of the implanted electronics package by the patient, by placement of an external magnet (not shown) in proximity to the implanted device. Other forms of manual activating means may be employed instead, such as a microphone for detecting taps by the patient on the skin directly over the stimulus generator, or a patient-triggered external RF signal generator.

The entire stimulus generator 10 is housed in a hermetically sealed, biologically compatible (biocompatible) titanium case indicated by the dotted line 70 (FIG. 1). Further details of suitable structure and operation of the neurostimulator, beyond those by which the device is adapted to treat the selected eating disorder as described herein, are available in the '985 application, to which the reader is referred.

In operation of the stimulus generator 10 to control and treat compulsive overeating (including binge eating), the pulsed signal from pulse generator 15 is applied to excitation/sensing electrodes 12-1, 12-2 via high impedance 17 and lead 20 (FIG. 3). The amplitude of the signal on these electrodes is a function of the impedance between them, which varies according to whether the esophagus 14 is empty or has food passing through it (and therefore, between the electrodes). The peak signal amplitude on electrodes 12 is detected and averaged by peak detector 22 over a predetermined interval of time. This may be calibrated to differentiate between different types of swallowing, such as of solids versus liquids and/or short swallows versus long swallows. The period of time in question may be selected according to the individual patient's eating habits.

The number and length of swallows occurring within the predetermined interval is detected by the esophageal electrode/detection system, and the sum of the swallows is calculated by processing to estimate the quantity of food consumed by the patient. The peak detector and averaging circuit 22 smooth each swallow derived from the parameters of the electrical signal on the lead/electrode system, and the comparator 30 detects the presence and length of the swallows from that information and information supplied by microprocessor 27 via D/A converter 33. The microprocessor, in turn, sums the number of swallows in the predetermined interval and compares that number to a programmed threshold value, representative of a known quantity of consumption. When the summed number reaches or exceeds the programmed threshold value, the microprocessor initiates the stimulation signal for application to the nerve electrode set 40 implanted on the vagus nerve, by selective activation of the output signal generator 36.

Alternatively, or in addition to the sensing electrodes 12 on the patient's esophagus, a set of bipolar electrodes 67 secured to the outer wall of the patient's stomach 13 (one at each of opposite sides as depicted in FIG. 3) may be utilized for purposes of measuring the amount of food in the stomach. The stomach electrodes would be connected via lead(s) 69, and selectively through a double pole switch 71 controlled by the microprocessor in the stimulus generator, to the pulse generator and the peak detector. The stomach impedance sensing electrode system and its operation is similar to that described above for the esophagus impedance sensing electrode system. However, the body generates digestive fluids in response to the presence of food, and hence, the impedance changes in the stomach are of a more complex nature than those observed at the esophageal electrodes. A combination of these sensing electrode systems, one on the esophagus and one on the stomach, may provide better data to the microprocessor than either alone, to more accurately determine the food intake and amount of food in the stomach. Such an arrangement, however, requires the use of the additional lead and electrode set (69, 67) for the stomach impedance sensing, and of the double pole switch 71 controlled by microprocessor 27 in the stimulus generator, and is not part of the preferred embodiment.

The detection system may be and preferably is calibrated by telemetry (via programming wand 47) to the implanted neurostimulator for each individual patient and the specific nature of the eating disorder. The results are then programmed into the microprocessor for the appropriate treatment.

As discussed above, the stimulus generator may also be activated manually by the patient by any of various means by appropriate implementation of the device. These techniques include the patient's use of an external magnet, or of an external RF signal generator, or tapping on the surface overlying the stimulus generator, to activate the neurostimulator and thereby cause the application of the desired modulating signal to the stimulating electrodes. Upon experiencing the compulsive craving, the obese or bulimic patient can simply voluntarily activate the stimulus generator. If the patient fails to act, the automatic detection of the overeating and consequent application of the necessary therapy will take place through modulation of vagal activity to produce the sensation of satiety.

Another form of treatment of compulsive overeating may be implemented by programming the stimulus generator to periodically deliver the vagal activity modulation productive of satiety at programmed intervals between prescribed normal mealtimes. This will tend to reduce excessive snacking between meals, which may otherwise be of insufficient quantity within a preset time interval to trigger automatic delivery of the therapy. It will be noted that the various techniques employed according to the methods and apparatus of the present invention are designed to treat the symptoms of the disorder rather than to target the root cause of the compulsive behavior. In essence, the patient is "tricked" into believing that the symptom of the eating disorder is not present, by the sensation of reducing or enhancing the appetite depending on the nature of the eating disorder being treated and the consequent programming of the stimulating signal parameters. Nevertheless, these types of treatment can be very beneficial, particularly in extreme cases.

Features may be incorporated into the neurostimulator for purposes of the safety and comfort of the patient. The patient's comfort would be enhanced by ramping the stimulus up during the first two seconds of stimulation. The device may also have a clamping circuit to limit the maximum voltage (14 volts for example) deliverable to the vagus nerve, to prevent nerve damage. An additional safety function may be provided by implementing the device to cease stimulation in response to manual deactivation through techniques and means similar to those described above for manual activation. In this way, the patient may interrupt the stimulation if for any reason it suddenly becomes intolerable.

The stimulating nerve electrode set or assembly 40 is shown in greater detail in FIG. 4. The electrode set is conductively connected to the distal end of a pair of insulated electrically conductive electrode leads 38 which are attached at the proximal end to the connector 65 (and thereby, to the output signal generating circuit 36) of the electronics package. Electrode set 40 comprises bipolar stimulating electrodes 40-1 and 40-2, preferably of the type described in U.S. Pat. No. 4,573,481 issued Mar. 4, 1986 to Bullara. The electrode assembly is surgically implanted around the vagus nerve 44 in the patient's abdomen just above the stomach. The two electrodes 40-1 and 40-2 are wrapped about the vagus nerve, and the assembly is secured to the nerve by a spiral anchoring tether 74 preferably as shown in U.S. Pat. No. 4,979,511 issued Dec. 25, 1990 to Reese S. Terry, Jr. and assigned to the same assignee as the instant application. Lead(s) 38 is secured, while retaining the ability to flex with movement of the chest and abdomen, by a suture connection 75 to nearby tissue.

The open helical design of electrode assembly 40 (described in detail in the above-cited Bullara patent), which is self-sizing and flexible, minimizes mechanical trauma to the nerve and allows body fluid interchange with the nerve. The electrode assembly conforms to the shape of the nerve, providing a low stimulation threshold by allowing a larger stimulation contact area. Structurally, the electrode assembly comprises two ribbons of platinum constituting the electrodes which are individually bonded to the inside surface of each of the first two spiral loops 40-1 and 40-2 of a three-loop helical assembly, and the two lead wires are respectively welded to the conductive ribbon electrodes. The remainder of each loop is composed of silicone rubber, and the third loop 74 acts merely as the tether for the electrode assembly. The inner diameter of the helical bipolar electrode assembly 40 may typically be approximately two millimeters (mm) and an individual spiral is about seven mm long (measured along the axis of the nerve).

The stimulus generator may be programmed with programming wand 47 and a personal computer 50 using suitable programming software developed according to the programming needs and signal parameters which have been described herein. The intention, of course, is to permit noninvasive communication with the electronics package after the latter is implanted, for both monitoring and programming functions. Beyond the essential functions, the programming software should be structured to provide straightforward, menu-driven operation, HELP functions, prompts, and messages to facilitate simple and rapid programming while keeping the user fully informed of everything occurring at each step of a sequence. Programming capabilities should include capability to modify the electronics package's adjustable parameters, to test device diagnostics, and to store and retrieve telemetered data. It is desirable that when the implanted unit is interrogated, the present state of the adjustable parameters is displayed on the PC monitor so that the programmer may then conveniently change any or all of those parameters at the same time; and, if a particular parameter is selected for change, all permissible values for that parameter are displayed so that the programmer may select an appropriate desired value for entry into the neurostimulator.

Other desirable features of appropriate software and related electronics would include the capability to store and retrieve historical data, including patient code, device serial number, number of hours of battery operation, number of hours of stimulation output, and number of magnetic activations (indicating patient intercession) for display on a screen with information showing date and time of the last one or more activations.

Diagnostics testing should be implemented to verify proper operation of the device, and to indicate the existence of problems such as with communication, the battery, or the lead/electrode impedance. A low battery reading, for example, would be indicative of imminent end of life of the battery and need for implantation of a new device. However, battery life should considerably exceed that of other implantable medical devices, such as cardiac pacemakers, because of the relatively less frequent need for activation of the neurostimulator of the present invention. In any event, the nerve electrodes are capable of indefinite use absent indication of a problem with them observed on the diagnostics testing.

Figure 5:
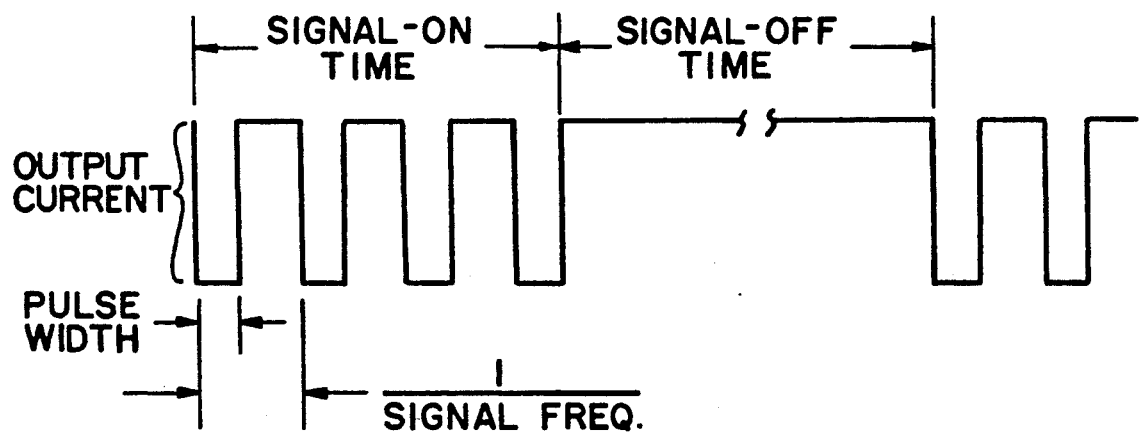
FIG. 5 is an illustrative idealized electrical output signal waveform of the stimulus generator useful for clarifying relevant parameters of the signal.

FIG. 5 illustrates the general nature, in idealized representation, of the output signal waveform delivered by output section 36 of the neurostimulator to electrode assembly 40. This illustration is presented principally for the sake of clarifying terminology, including the parameters of output signal on-time, output signal off-time, output signal frequency, output signal pulse width, and output signal current. Such parameters are discussed below in terms of ranges of values and typical values of the output signal which may be programmed into the device for treatment of various eating disorders.

For the obese patient, the stimulation strategy programmed into the neurostimulator is to provide modulation through the medium of the stimulating signal which is appropriate to increase vagal activity before and during meal periods. In the preferred embodiment and method of the invention, the stimulus generator output signal may be patient activated, but means are provided to detect eating, as the distension of and presence of food in the esophagus during swallowing and to integrate the number of swallows over time to detect the amount of food consumed, and when that amount exceeds a predetermined quantity in the selected time interval, to trigger automatic activation of the output signals from the electronics package.

The preferred range of stimulation parameters of the output signal for treatment and control of eating disorders, and the nominal value of each parameter programmed into the device by the attending physician are set forth in the following table.

|  | Range | Typical |
| --- | --- | --- |
| Pulse Width | 0.05–1.5 ms | 0.5 ms |
| Output Current | 0.1–5.0 mA | 1.5 mA |
| Frequency | 5–150 Hz | 25 Hz |
| On Time | 300–10,000 sec | 300 sec |
| Off Time | 300–30,000 sec | 1000 sec |
| Frequency Sweep? | 10–50 Hz | Yes (optional) |
| Random frequency? | 10–50 Hz | Yes (optional) |

The device may utilize circadian or other programming as well, so that activation occurs automatically at normal mealtimes for this patient. This may be in addition to the provision for the manual, periodic between meal, and sensing-triggered activation as described above herein. The treatment induces appetite suppression in obese patients and contributes ultimately to weight reduction, by controlling (producing the sensation of) satiety in the patient.

For bulimia patients, the device is programmed in the same manner as above, so that when triggered, vagal activity is increased and the patient's appetite is suppressed by a feeling of fullness. Manual activation by the patient is desirable, but because the psychological pattern is difficult to control, the use of circadian programming and detection of overeating by measuring quantity of food consumed during a given interval serves as an important backup in the therapeutic modality. It is also desirable to decrease vagal activity at other times to provide some smoothing out of eating.

In the treatment of anorexia nervosa patients, the programming is set to modulate vagal activity to considerably enhance the patient's appetite and the urge to eat, or at least to suppress satiety. Here also, the device may be manually activated, automatically activated upon detection of the condition of "emptiness" of the stomach or of exceeding a certain period since the last swallowing of food, or activated according to the patient's circadian cycle to induce hunger (or suppress satiety) at normal mealtimes, or by a combination of such activations.

As noted earlier herein, inhibition or blocking of signals on the vagus nerve is a potential strategy for treating or controlling an eating disorder such as anorexia nervosa. However, vagal stimulation generates a signal on the nerve, and the stomach signals are carried by the small C fibers which become refractory if stimulated at high frequency (for example, 40 Hz or higher) for more than a period of 30 to 60 seconds. Therefore, a strategy for inhibiting or blocking this C-fiber information is to stimulate the high frequencies with on-time of, say, 300 seconds and off-time of about 20 seconds. This sequence would be repeated for the interval of time that control (blocking of the C-fiber information) is desired to be exercised.

Alternatively, because C fibers become refractory if stimulated for a sufficiently long period, another strategy would be to continuously stimulate the C fibers to render them refractory and thereby block the nerve signals from getting through. The signals of interest are believed to be conducted principally if not solely on the C fibers. These fibers are slow to conduct compared to the A and B fibers, but the slower response is acceptable here. An important aspect is the programming of stimulation parameters which block vagal activity despite the speed of conduction of the nerve.

Although certain preferred embodiments and methods of treating and controlling eating disorders through vagal modulation according to the invention have been described herein, it will be apparent to those skilled in the field from a consideration of the foregoing description that variations and modifications of such embodiments, methods and techniques may be made without departing from the true spirit and scope of the invention. For example, although a totally implantable device is preferred, the electronic energization package may, if desired, be primarily external to the body. Stimulation can be achieved with RF power device providing the necessary energy level. The implanted components could be limited to the lead/electrode assembly, a coil and a DC rectifier. With such an arrangement, pulses programmed with the desired parameters are transmitted through the skin with an RF carrier, and the signal is thereafter rectified to regenerate a pulsed signal for application as the stimulus to the vagus nerve to modulate vagal activity. This would virtually eliminate the need for battery changes.

However, the external transmitter must be carried on the person of the patient, which is inconvenient. Also, detection is more difficult with a simple rectification system, and greater power is required for activation than if the system were totally implanted. In any event, a totally implanted system is expected to exhibit a relatively long service lifetime, amounting potentially to several years, because of the relatively small power requirements for most eating disorder treatment applications. Also, as noted earlier herein, it is possible, although considerably less desirable, to employ an external stimulus generator with leads extending percutaneously to the implanted nerve electrode set. The major problem encountered with the latter technique is the potential for infection. Its advantage is that the patient can undergo a relatively simple procedure to allow short term tests to determine whether the eating disorder of this particular patient is amenable to successful treatment. If it is, a more permanent implant may be provided.

Accordingly, it is intended that the invention shall be limited only to the extent required by the appended claims and the rules and principles of applicable law.

What is claimed is:

1. A method of treating patients with eating disorders by use of a therapy which alleviates a symptom of the disorder, which comprises the steps of:
   detecting a preselected event indicative of an imminent need for treatment of the specific eating disorder of interest, and
   responding to the detected occurrence of the preselected event by applying a predetermined stimulating signal to the patient's vagus nerve appropriate to alleviate said symptom of the eating disorder of interest.

2. The method of claim 1, wherein
the preselected event is a specified level of food consumption by the patient within a set interval of time.

3. The method of claim 2, wherein
the occurrence of said preselected event is detected by summing the number of swallows of food by the patient within said set interval of time.

4. The method of claim 1, wherein
the preselected event is the passage of each of a sequence of preset intervals of time.

5. The method of claim 1, wherein
the preselected event is the patient's own recognition of the need for treatment by voluntarily initiating the application of said predetermined stimulating signal to the vagus nerve.

6. The method of claim 1, wherein
the disorder is compulsive eating to excess, and
said stimulating signal is predetermined to produce a sensation of satiety in the patient.

7. The method of claim 1, wherein
said stimulating signal is applied to the patient's vagus nerve by a nerve electrode implanted on the nerve in the vicinity of the patient's stomach.

8. Apparatus for treating patients with eating disorders by application of a modulating signal to the patient's vagus nerve to stimulate or inhibit neural impulses and produce excitatory or inhibitory neurotransmitter release by the nerve according to the specific nature of the eating disorder, comprising:
   neurostimulator means for generating an electrical output signal in response to activation thereof, said neurostimulator means including
   sensing means for detecting the occurrence of a selected event indicative of the need for imminent treatment of the eating disorder, and including activating means responsive to the detection for activating said neurostimulator means, and
   lead/electrode means responsive to generation of the electrical output signal by said neurostimulator means for application thereof as said modulating signal to the patient's vagus nerve.

9. The invention of claim 8, wherein
said neurostimulator means further includes:
   programming means for selectively programming the parameters of the electrical output signal of said neurostimulator means according to the nature of the eating disorder being treated, within respective predetermined ranges.

10. The invention of claim 8, wherein
said neurostimulator means further includes:
    means for calibrating the neurostimulator means according to the specific patient and the specific eating disorder being treated.

11. The invention of claim 8, wherein
said sensing means comprises timer means for selective setting to prescribed normal mealtimes for the patient as the event to be detected.

12. The invention of claim 8, wherein
said sensing means comprises timer means for detecting the passage of each of a sequence of time intervals as the event to be detected.

13. The invention of claim 8, wherein
said sensing means comprises means for detecting the consumption of food by the patient within a predetermined interval of time.

14. The invention of claim 13, wherein
the detecting means comprises
    means for summing the number of swallows of food by the patient within said predetermined interval of time, and
    means for comparing the summed number with a number indicative of threshold level of food consumption.

15. The invention of claim 8, wherein
said sensing means comprises means for detecting voluntary triggering of said activating means by the patient as the event to be detected.

16. The invention of claim 8, wherein
said lead/electrode means includes nerve electrode means and means for securing said nerve electrode means to the patient's vagus nerve in the vicinity of the stomach.

17. The invention of claim 8, wherein
said neurostimulator means is arranged and adapted to be implanted in the patient's body.

18. A neurostimulator for treatment of eating disorders in human patients, comprising
    an implantable electrical signal generator,
    programming means for selectively programming the parameters of the electrical signal generated by the generator to modulate electrical activity of the patient's vagus nerve to evoke different sensations by the patient according to the nature of the eating disorder being treated, means for applying the generated signal to the patient's vagus nerve, and means for detecting a symptom of the eating disorder being treated to activate the generation of the programmed electrical signal by the generator.

19. A method for treating and controlling compulsive eating disorders characterized by compulsive action exhibited by the individual suffering from the disorder, which comprises the steps of:

detecting a known symptom of the eating disorder of interest indicative of imminent need for intervention to control the disorder, and responding to the detected occurrence of said symptom by modulating the vagal activity of the individual suffering the eating disorder to treat the symptom and deter the compulsive action associated with the disorder.

* * * * *